United States Patent [19]

Batt et al.

[11] Patent Number: 5,049,570
[45] Date of Patent: Sep. 17, 1991

[54] PYRIDYLPHENYL NITROGEN HETEROCYCLE-SUBSTITUTED CARBINOLS AND DERIVATIVES THEREOF WITH ANTI-INFLAMMATORY ACTIVITY

[75] Inventors: Douglas G. Batt; Stephen W. Wright, both of Wilmington, Del.

[73] Assignee: Du Pont Merck Pharmaceutical Company, Wilmington, Del.

[21] Appl. No.: 469,854

[22] Filed: Jan. 23, 1990

[51] Int. Cl.$^5$ ............... A61K 31/44; C07D 401/10
[52] U.S. Cl. ................................. 514/341; 514/333; 514/338; 514/339; 514/342; 514/343; 514/340; 514/318; 546/275; 546/280; 546/284; 546/283; 546/276; 546/271; 546/273; 546/279; 546/194; 546/278; 546/256

[58] Field of Search .............. 546/278, 256, 194; 514/341, 333, 318

[56] References Cited

U.S. PATENT DOCUMENTS 4,301,166 11/1981 Regel et al. .................. 514/383
4,859,693 8/1989 Batt et al. .................... 514/397

FOREIGN PATENT DOCUMENTS 1145253 4/1983 Canada .
2920375 11/1980 Fed. Rep. of Germany .

Primary Examiner—Jane T. Fan

[57] ABSTRACT

Pyridylphenyl nitrogen heterocycle-substituted carbinols and derivatives thereof and pharmaceutical compositions containing such compounds are useful for treating inflammatory diseases in mammals.

54 Claims, No Drawings

PYRIDYLPHENYL NITROGEN HETEROCYCLE-SUBSTITUTED CARBINOLS AND DERIVATIVES THEREOF WITH ANTI-INFLAMMATORY ACTIVITY

BACKGROUND OF THE INVENTION

1. Field of the Invention

This invention relates to pyridylphenyl nitrogen heterocycle-substituted carbinols, pharmaceutical compositions containing them, methods of using them to treat inflammatory disease in mammals and processes for preparing said compounds.

2. Background

Inflammatory diseases are a widespread cause of human suffering and loss of function. Additionally, the treatment of patients with these diseases represents a very large expense in terms of money, facilities and personnel. The incidence of many such diseases is expected to rise in the future as life expectancy and the median age of the population continue to increase.

Inflammatory diseases are known which affect many diverse tissues and organs in the body. Examples of diseases in which the inflammation is most apparent in the joints and related connective tissue are diseases such as osteoarthritis, rheumatoid arthritis, tendonitis and bursitis. These diseases are most often treated with non-steroidal anti-inflammatory agents such as aspirin, ibuprofen, and piroxicam, or with anti-inflammatory glucocorticosteroids. However, these treatments are deficient either due to a lack of efficacy in completely controlling the disease process, or due to unacceptable toxic side effects. Rheumatoid arthritis in particular is a representative of a class of systemic diseases thought to possess an auto-immunity component, which are treated additionally with anti-proliferative agents and with so-called disease-modifying agents such as gold salts, penicillamine and antimalarial agents. These drugs also possess severe toxic effects which limit their utility.

Examples of diseases in which the inflammation is most apparent in the skin are psoriasis, contact dermatitis, atopic dermatitis, and eczema. These diseases are usually treated with anti-inflammatory glucocorticosteroids, or (in the case of psoriasis) with psoralen in combination with UV-A light (PUVA), or with coal tar preparations or antiproliferative agents. Again, these treatments are often unacceptable to patients and also have a poor degree of efficacy and/or unacceptable side effects.

Inflammatory diseases of other tissues and organs are also of concern, for example inflammatory bowel disease and ocular inflammation such as uveitis and conjunctivitis. Treatments for these diseases, primarily using glucocorticosteroids, also lack efficacy and freedom from toxic effects.

Thus, there is a continuing medical need for safe, efficacious anti-inflammatory agents for use as systemic and/or topical therapy for inflammatory diseases.

PRIOR ART

Commonly assigned U.S. Pat. No. 4,859,693 discloses the anti-inflammatory activity of carbinoloimidazoles with the structure

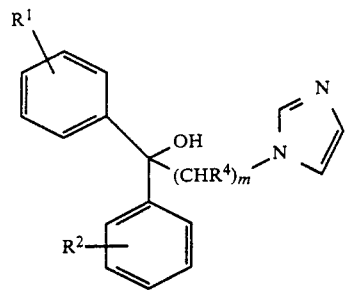

wherein $R^1$ and $R^2$ are H, F, Cl, Br, $CH_3$, $CF_3$, or $S(O)nR^3$ (n=0, 1, or 2); $R^3$ is $C_1$–$C_4$ alkyl; m is 1 to 3; and $R^4$ is H or $C_1$–$C_4$ alkyl, provided that when $R^4$ is alkyl then m is 1.

German Patent No. 2920375 and U.S. Pat. No. 4,301,166 disclose, inter alia, fungicidal compounds with the structure

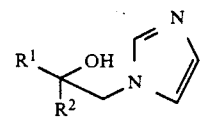

wherein $R^1$ is optionally substituted phenyl and $R^2$ is optionally substituted biphenyl. German Patent No. 2920374 discloses compounds of the same structure except that the imidazole group is replaced with triazole. These triazoles also have fungicidal activity.

None of the above-described references disclose the compounds of the present invention or suggest that such compounds would possess activity as anti-inflammatory agents.

SUMMARY OF THE INVENTION

According to the present invention provided are compounds having the formula:

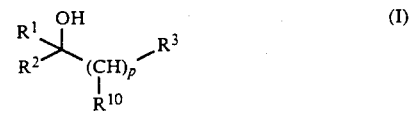

in the form of an individual stereoisomer, a non-racemic stereoisomer mixture or a racemic mixture or a pharmaceutically acceptable salt thereof wherein:
$R^1$ is 2-, 3-, or 4-pyridyl,

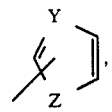

$R^7$, or phenyl optionally substituted with 1–3 substituents independently selected from the group consisting of F, Cl, Br, $C_1$-$C_4$ alkyl, $C_1$-$C_4$ perfluoroalkyl, $C_1$-$C_4$ alkylthio, $C_1$-$C_4$ alkylsulfonyl, CHO, $COOR^4$, $C_1$-$C_4$ acyl, $NR^5R^6$, $C_1$-$C_4$ alkoxy or $CH_2OR^8$;

$R^2$ and $R^7$ independently are phenyl substituted in the ortho, meta, or para position with $R^9$;

$R^3$ is imidazole, 1,2,4-triazole, 1,3,4-triazole, benzimidazole, pyrrole, indole, or pyrazole provided that $R^3$ is bonded to the remainder of the structure through a nitrogen atom;

$R^4$, $R^8$, and $R^{10}$ independently are H or $C_1$-$C_4$ alkyl;

$R^5$ and $R^6$ independently are H, $C_1$-$C_4$ alkyl, or taken together are $(CH_2)m$ wherein m is 4-5;

$R^9$ is 2-, 3-, or 4-pyridyl;

Y is N or CH;

Z is S, O, or $NR^{11}$;

$R^{11}$ is H or $C_1$-$C_4$ alkyl; and p is 1-4 provided that when p is greater than 1, then $R^{10}$ is H.

Also provided are pharmaceutical compositions comprising compounds of Formula I as individual stereoisomers, non-racemic stereoisomer mixtures, racemic mixtures or pharmaceutically acceptable salts thereof and a pharmaceutically acceptable carrier.

Further provided are methods of using compounds of Formula I to treat an inflammatory disease in a mammal.

Additionally provided are processes for preparing the compounds of Formula I as described hereinafter.

PREFERRED EMBODIMENTS

Preferred compounds are those compounds of Formula I as described above wherein:

(a) p is 1; and/or (b) $R^3$ is imidazole or triazole.

More preferred compounds are those preferred compounds wherein:

(a) $R^3$ is imidazole; and/or (b) $R^{10}$ is H; and/or (c) $R^1$ is phenyl optionally substituted by one or two of the substituents listed above.

Most preferred compounds are those more preferred compounds wherein:

(a) $R^1$ is mono- or di-substituted phenyl with one of the substituents at the 4-position; and/or (b) $R^2$ is 4-(4-pyridyl)phenyl) or 3-(4-pyridyl)phenyl).

Specifically preferred compounds are:

a) 1-(4-fluorophenyl)-1-[4-(4-pyridyl)phenyl]-2-(1-imidazolyl)ethanol.

b) 1-(2,4-difluorophenyl)-1-[4-(4-pyridyl)phenyl]-2-(1-imidazolyl)ethanol.

c) 1-(4-fluorophenyl)-1-[3-(4-pyridyl)phenyl]-2-(1-imidazolyl)ethanol.

d) 1-(4-methylphenyl)-1-[4-(4-pyridyl)phenyl]-2-(1-imidazolyl)ethanol.

e) 1-(4-methoxyphenyl)-1-[4-(4-pyridyl)phenyl]-2-(1-imidazolyl)ethanol.

f) 1-(4-trifluoromethylphenyl)-1-[4-(4-pyridyl)phenyl]-2-(1-imidazolyl)ethanol.

g) 1-(4-chlorophenyl)-1-[4-(4-pyridyl)phenyl]-2-(1-imidazolyl)ethanol.

DETAILED DESCRIPTION OF THE INVENTION

The compounds of Formula (I) can be prepared using the reactions and techniques described below. The reactions are usually performed in a solvent appropriate to the reagents and materials employed, and suitable for the transformation being effected. In some cases functional groups on the starting materials may need to be protected by standard protecting groups reported in the chemical literature which are well known to one skilled in the art. In some cases, substituents on the starting materials may be incompatible with some of the reaction conditions required in some of the methods described. Such restrictions to the substituents which are compatible with the reaction conditions will be readily apparent to one skilled in the art and alternative methods described herein must then be used.

Many of the compounds of Formula (I) possess one or more chiral carbon atoms, allowing the occurrence of different enantiomers and/or diastereomers. In those cases where enantiomers are possible, the separate enantiomers may be obtained in pure or enantiomerically enriched form either by starting from a single enantiomer of a starting material (in those cases where the starting material also possesses the chiral carbon atom), or by resolution of the racemic mixture using standard methods. Diastereomers may generally also be separated using standard methods such as chromatography or fractional crystallization.

The compounds of Formula (I) may be converted to acid addition salts by treatment with a suitable pharmaceutically acceptable acid, using standard methods.

Several methods may be used to prepare the compounds of Formula (I). In Method A (Scheme 1), a bromophenyl compound (II) may be reacted with a pyridylstannane ($R^9SnR$, where $R=C_1$-$C_4$ alkyl) such as a pyridyltrimethylstannane in the presence of an appropriate transition metal catalyst to provide the desired compound of Formula (I). Examples of suitable catalysts are complexes of palladium and nickel, such as bis(triphenylphosphine) palladium(II) chloride. The reactions are usually conducted in a suitable organic solvent or solvent mixture such as tetrahydrofuran, N,N-dimethylformamide, or mixtures of N,N-dimethylformamide and an amine such as triethylamine. The reactions are usually conducted at temperatures above room temperature but below the boiling point of the solvent, preferably between about 50° and 100° C. An example of such a transition-metal mediated coupling between a pyridylstannane and a substituted bromobenzene from the chemical literature is given by Bailey, *Tetrahedron Lett.* 1986, 27, 4407. The starting materials for this method are known in the chemical literature, or may be prepared using known methods. Bromophenyl compounds of formula (II) may be prepared, for example, using methods disclosed by commonly assigned U.S. Pat. No. 4,859,693. Trimethylstannylpyridines have also been reported in the chemical literature, for example by Yamamoto and Yanagi, *Heterocycles* 1981, 16, 1161. Method A is exemplified by the procedure of Example 1.

SCHEME 1

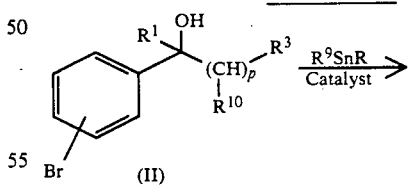

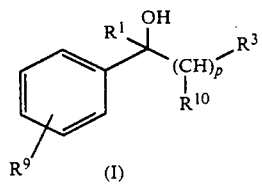

A second method (Method B) for preparing those compounds of Formula (I) wherein p is 1 is shown in Scheme 2. A pyridylphenyl ketone of formula (III) may be converted to the alpha-halo derivative (IV) where X is bromine or chlorine. These transformations are well known in the chemical literature, and may be performed using reagents such as bromine or chlorine in the presence of an acidic catalyst such as hydrobromic acid. A useful solvent for these reactions is acetic acid. The halo-derivative (IV) may then be reacted with a nitrogen heterocycle R³H or with a metal salt of a heterocycle R³M where M is, for example, sodium or potassium to give the substituted compound (V). The nitrogen heterocycle may be converted to the metal salt and subsequently be reacted with the compound of formula (IV), or the nitrogen heterocycle may be combined with a suitable base such as potassium tert-butoxide directly in the reaction mixture to form the metal salt in situ. The desired compound of formula (I) may be prepared from the intermediate of formula (V) by treatment with an organometallic compound R¹M¹, where M¹ may be, for example, lithium, magnesium halide, or cerium halide. Organocerium halides are preferred for this reaction, since hydrogen abstraction from (V), which leads to recovered starting material, is often minimized by the use of these reagents. The general method of preparation of 1,1-diaryl-2-azolylethanols and derivatives by organometallic addition to an aryl azolylmethyl ketone has been disclosed previously, for example, in U.S. Pat. No. 4,301,166 and U.S. Pat. No. 4,689,337. Method B is exemplified by the procedure of Example 21.

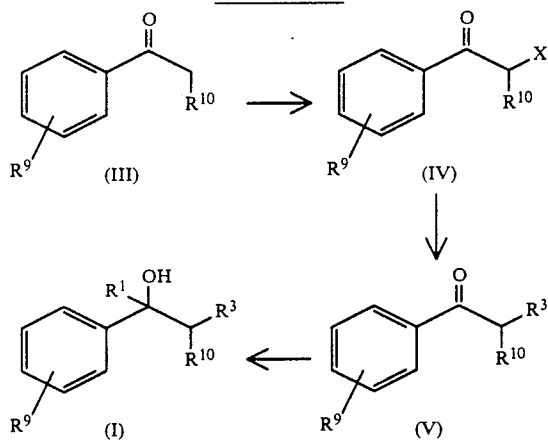

SCHEME 2

Another method (Method C) for preparing those compounds of Formula (I) wherein p is 1 is shown in Scheme 3. A pyridylphenyl ketone of formula (III) may be reacted with an aryl organometallic reagent such as an arylmagnesium halide or aryllithium reagent to provide the tertiary alcohol of formula (VI). Dehydration of this alcohol to the olefin of formula (VII) may be performed using standard chemical techniques, for example by treatment with an acid catalyst and azeotropic removal of the water formed in the reaction. The olefin may be converted to the vicinal diol of formula (VIII) using standard oxidation techniques, for example, by treatment with osmium tetroxide, optionally in the presence of an auxiliary oxidant such as N-methylmorpholine N-oxide. The compound of formula (VIII) may be converted to the desired compound of formula (I) by conversion of the less sterically-hindered alcohol to a better leaving group, for example by conversion to a sulfonate ester such as the methanesulfonate ester, using well known methods. This intermediate may then be reacted with a nitrogen heterocycle R³H, or with a metal salt of a nitrogen heterocycle R³M where M is, for example, sodium or potassium. The nitrogen heterocycle may be converted to the metal salt and subsequently be reacted with the compound of formula (VIII), or the nitrogen heterocycle may be combined with a suitable base such as potassium tert-butoxide directly in the reaction mixture to form the metal salt in situ. (The general method for converting a diaryl alkanediol such as (VIII) to a diarylimidazolylethanol such as (I) is disclosed in U.S. Pat. No. 4,859,693.) Method C is exemplified by the procedure of Example 41.

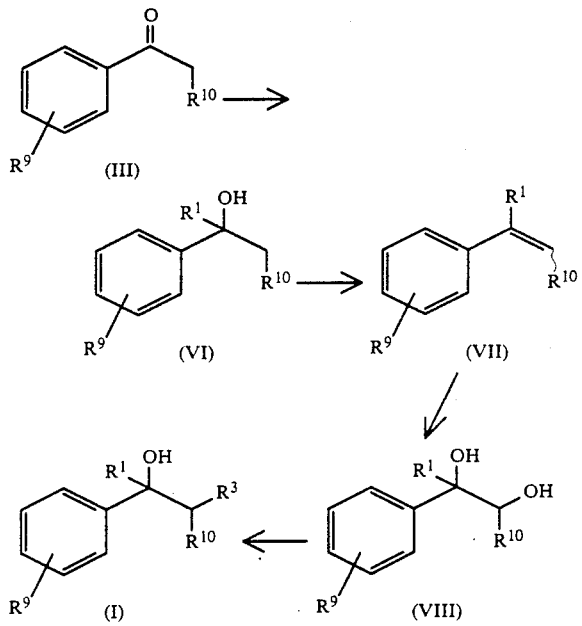

SCHEME 3

Certain substituents on R¹ in compounds of Formula (I) wherein R¹ is substituted phenyl may be prepared from other compounds of Formula (I) by standard chemical manipulations of substituents which are well known to one skilled in the art. The preparation of a compound of Formula (I) by functional group manipulation of another compound of Formula (I) is demonstrated by Examples 61 and 62.

The pyridylphenyl ketones which are starting materials for Methods B and C may be prepared from bromophenyl ketones or iodophenyl ketones of formula (IX), wherein X is Br or I, as shown in Scheme 4. The ketone of formula (IX) may be first converted to a protected form of the ketone by treatment with a primary alcohol in the presence of an aliphatic orthoester of this alcohol and an acid catalyst, using standard methods. Depending on the nature of the ketone (IX), either the ketal (X) or the enol ether (XI) may be obtained. Both of these are suitable for use in the subsequent reaction. The protected ketone of formula (X) or (XI) may then be converted to an organometallic derivative such as the magnesium halide or lithium derivative using standard methods. This organometallic reagent may be used directly, or may preferably be further converted by transmetallation to a different organometallic derivative such as the organozinc reagent, which is more suitable for use in the subsequent coupling reaction. The organometallic reagent may then be treated with a halopyridine in the presence of a transition metal catalyst, such as a nickel or palladium catalyst, to provide after acid hydrolysis the corresponding compound of formula (III). (An example of forming an unsymmetrical biaryl using the nickel- or palladium-catalyzed coupling of an arylzinc reagent with an aryl halide has been reported by Negishi et al., *J. Org. Chem.* 1977, 42, 1821.)

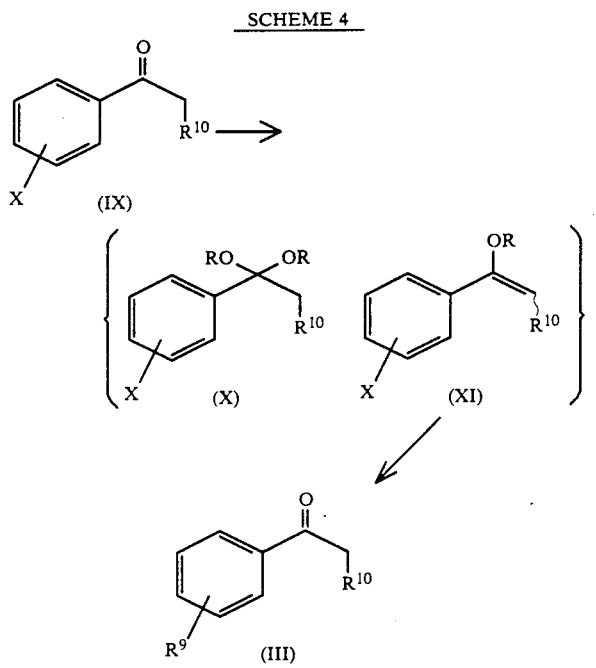

SCHEME 4

Examples of the preparation of pyridylphenyl ketone starting materials are given below. All temperatures are in degrees Celsius. All reactions are performed under an atmosphere of dry nitrogen. Concentration under reduced pressure is performed with a rotary evaporator using a water aspirator. Nuclear magnetic resonance (NMR) spectra were obtained at a field strength of 200 or 300 MHz; abbreviations for NMR data are as follows: s=singlet, d=doublet, m=multiplet, $CDCl_3$=deuterochloroform solvent. Peak positions for NMR data are reported as parts per million downfield from the internal standard tetramethylsilane. All parts and percentages are by weight unless otherwise indicated.

Preparation of Pyridylphenyl Ketone Starting Materials

Preparation of 3-(2-Acetylphenyl)pyridine a. A mixture of 2'-bromoacetophenone (75.0 g, 0.375 mol), trimethyl orthoformate (210 mL, 1.91 mol), methanol (210 mL), and Dowex® 50X2-400 acid ion exchange resin (7.5 g) was heated at reflux for 1.5 h. The mixture was cooled, filtered through Celite®, and concentrated. Vacuum distillation of the residue gave 1-methoxy-2'-bromostyrene (71.66 g, 90%); NMR ($CDCl_3$) 7.8–7.1 (4H), 4.40 (d, 1H), 4.30 (d, 1H), 3.75 (s, 3H). A solution of this material (1.84 g, 7.5 mmol) in tetrahydrofuran (10 mL) was cooled to −78° and treated over 4 min with tert-butyllithium (1.7 M in pentane; 8.8 mL, 15 mmol). After stirring for 30 min, the solution was warmed to 0° and added by cannula to a slurry of zinc chloride (freshly fused and powdered; 1.02 g, 7.5 mmol) in tetrahydrofuran (15 mL) at 0°. The mixture was stirred for 60 min at room temperature. In a separate flask, a suspension of bis(triphenylphosphine)palladium (II) chloride (0.165 g, 0.23 mmol) in tetrahydrofuran (7.5 mL) was treated with diisobutylaluminum hydride (1.0 M in toluene; 0.50 mL, 0.50 mmol). The organozinc solution was added to the palladium catalyst mixture by cannula, and the resulting mixture was treated with 3-bromopyridine (0.72 mL, 7.5 mmol). The mixture was stirred at room temperature overnight, and was concentrated. The residue was partitioned between ether and 6 M aqueous sodium hydroxide. The ether layer was washed with water and brine, then was dried over magnesium sulfate and concentrated to give a yellow oil. This was stirred in 1 N hydrochloric acid (5 mL) and tetrahydrofuran (10 mL) at room temperature for 1 h. The mixture was concentrated, and the aqueous residue was washed with 1:1 hexane/ether. The aqueous phase was made basic with potassium hydroxide and extracted with methylene chloride. Drying over magnesium sulfate and concentration provided the title product as a yellow oil (1.33 g, 90%); NMR ($CDCl_3$) 8.65 (m, 2H), 7.70–7.25 (6H), 2.20 (s, 3H).

Preparation of 4-(2-Acetylphenyl)pyridine b. Using the same procedure, the title compound was prepared in 66% yield. NMR ($CDCl_3$) 8.65 (m, 2H), 7.66–7.25 (6H), 2.23 (s, 3H).

Preparation of 2-(2-Acetylphenyl)pyridine c. Using the same procedure, the title compound was prepared in 29% yield. NMR ($CDCl_3$) 8.65 (m, 2H), 7.8–7.25 (6H), 2.20 (s, 3H).

Preparation of 4-(4-Acetylphenyl)pyridine d. Using the same procedure, 4'-bromoacetophenone was converted to 1-(4-bromophenyl)-1,1-dimethylethane as a colorless liquid in 72% yield; NMR ($CDCl_3$) 7.55–7.30 (4H), 3.15 (s, 6H), 1.50 (s, 3H). This material was converted to the title compound in 97% yield: MP 94° C.; NMR ($CDCl_3$) 8.75 (d, 2H), 8.10 (d, 2H), 7.70 (d, 2H), 7.50 (d, 2H), 2.65 (s, 3H).

The preparation of the compounds of Formula (I) by Methods A through C is described in greater detail in Examples 1 to 62. In these examples, all temperatures are in degrees Celsius. All reactions are performed under an atmosphere of dry nitrogen. Concentration under reduced pressure is performed with a rotary evaporator using a water aspirator. Chromatography refers to the method of medium-pressure column chromatography described by Still et al., *J. Org. Chem.* 1978, 43, 2923. The composition of solvent mixtures used as chromatographic eluents are given in percentages by volume. Nuclear magnetic resonance (NMR) spectra were obtained at a field strength of 200 or 300 MHz; abbreviations for NMR data are as follows: s=singlet, d=doublet, dd=doublet of doublets, t=triplet, m=multiplet, $CDCl_3$=deuterochloroform solvent, DMSO-$d_6$=deutero-dimethylsulfoxide solvent, MeOH-$d_4$=deuteromethanol solvent. Peak positions for NMR data are reported as parts per million downfield from the internal standard tetramethylsilane. Mass spectra were obtained using methane chemical ionization; data are reported as the ratio of charge to mass of the parent ion.

EXAMPLE 1

Preparation of
1-(4-Flurophenyl)-1-[4-(4-pyridyl)phenyl-2-(1-imidazolyl)ethanol

A mixture of 1-(4-fluorophenyl)-1-(4-bromophenyl)-dazolyl)ethanol (4.0 g, 0.011 mol), 4-pyridyltrimethylstannane (4.02 g, 0.016 mol), and bis(triphenylphosphine) palladium(II) chloride (0.7 g, 0.001 mol) was combined in 10:1 N,N-dimethylformamide/triethylamine (40 mL) and heated at 70° for 72 h. The mixture was cooled to room temperature, filtered through Celite ® and the filter rinsed with methylene chloride. The filtrate was concentrated and the residue was dissolved in methylene chloride. The organic phase was washed with water and extracted with 1N hydrochloric acid. The acid extract was washed with ether and made basic with concentrated aqueous ammonia. The mixture was extracted with methylene chloride, the organic phase was washed with water, dried over magnesium sulfate and concentrated. The residue was chromatographed (9:1 methylene chloride/methanol) and the crude product was triturated in ether/hexane to provide the title product as a solid in 23% yield. MP 206–208°; NMR (CDCl$_3$) 8.65 (d, 2H), 7.72–6.92 (13H), 6.60 (d, 2H), 4.68 (s, 2H); Mass spec 360; Calcd. for $C_{22}H_{18}FN_3O$: C-72.84, H-4.96, N-11.58; Found: C-72.73, H-5.05, N-11.56.

Additional compounds of Formula (I) which were or may be prepared using the method of Example 1 are shown in Table 1.

TABLE 1

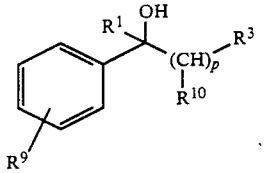

| Ex. # | R$^1$ | R$^9$ | R$^3$ | (CHR$^{10}$)$_p$ | mp (°C.) |
|---|---|---|---|---|---|
| 1 | 4-F-ph | 4-(4-pyr) | 1-imdz | CH$_2$ | 206–208 |
| 2 | 2,4-F$_2$-ph | 4-(2-pyr) | 1-imdz | CH$_2$ | 190–192 |
| 3 | 4-F-ph | 4-(2-pyr) | 1-imdz | CH$_2$ | 206–208 |
| 4 | 2,4-F$_2$-ph | 4-(3-pyr) | 1-imdz | CH$_2$ | 202–203 |
| 5 | 2,4-F$_2$-ph | 4-(4-pyr) | 1-imdz | CH$_2$ | 190–191 |
| 6 | 4-F-ph | 3-(2-pyr) | 1-imdz | CH$_2$ | 172–173 |
| 7 | 4-F-ph | 3-(3-pyr) | 1-imdz | CH$_2$ | 196–197 |
| 8 | 4-F-ph | 3-(4-pyr) | 1-imdz | CH$_2$ | 174–175 |
| 9 | C$_6$H$_5$ | 4-(4-pyr) | 1-imdz | CH$_2$ | 183–185 |
| 10 | 2-Cl-ph | 4-(4-pyr) | 1-imdz | CH$_2$ | 212–214 |
| 11 | 4-CH$_3$-ph | 4-(4-pyr) | 1-imdz | CH$_2$ | 184–186 |
| 12 | 4-CH$_3$O-ph | 4-(4-pyr) | 1-imdz | CH$_2$ | 202–203 |
| 13 | 4-F-ph | 4-(4-pyr) | 1-imdz | (CH$_2$)$_2$ | |
| 14 | 4-F-ph | 4-(4-pyr) | 1-imdz | (CH$_2$)$_4$ | |
| 15 | 4-F-ph | 4-(4-pyr) | 1-imdz | CHCH$_3$ | |
| 16 | 4-F-ph | 4-(4-pyr) | 1-imdz | CH(C$_4$H$_9$) | |
| 17 | 2-thienyl | 4-(3-pyr) | 1-imdz | CH$_2$ | |
| 18 | 4-CH$_3$OCH$_2$-ph | 3-(4-pyr) | 1-(1,2,4-tz) | CH$_2$ | |
| 19 | 4-Cl-ph | 4-(2-pyr) | 1-imdz | CHCH$_3$ | |

TABLE 1-continued

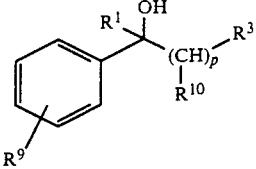

| Ex. # | R$^1$ | R$^9$ | R$^3$ | (CHR$^{10}$)$_p$ | mp (°C.) |
|---|---|---|---|---|---|
| 20 | 2-thiazolyl | 3-(3-pyr) | 1-imdz | CH$_2$ | |

Footnotes for Table 1
ph = phenyl; pyr = pyridyl; imdz = imidazolyl; tz = triazolyl

EXAMPLE 21

Preparation of
1-(4-Trifluoromethylphenyl)-1-[4-pyridyl)phenyl]-2-(1-imidazolyl)ethanol

Part A

A solution of 4-(4-acetylphenyl)-pyridine (9.85 g, 0.05 mol) in acetic acid (500 mL) was treated with a 30% solution of hydrogen bromide in acetic acid (50 mL) and warmed to 75° to dissolve the resulting precipitate. The solution was cooled to 35°, and treated slowly with a solution of bromine in acetic acid (1.0 M; 50 mL, 0.05 mol). The mixture was then stirred for 30 min, warmed to 70° for 5 min, cooled to room temperature and stirred overnight. The mixture was concentrated and the residue was twice taken up in toluene and re-concentrated. The residue (17.4 g, 97%) was 2-bromo-4'-(4-pyridyl)-acetophenone hydrobromide. MP>250°; NMR (MeOH-d$_4$) 8.90 (broad, 2H), 8.37 (d, 2H), 8.26 (d, 2H), 8.10 (d, 2H), 4.72 (S, 2H); Mass spec 358.

Part B

A slurry of the product of Part A (35.0 g, 0.098 mol) in tetrahydrofuran (300 mL) was treated with a solution of imidazole (40.0 g, 0.588 mol) in tetrahydrofuran (100 mL) and stirred at room temperature for 2 h. The mixture was concentrated and the residue was partitioned between water and methylene chloride. The aqueous layer was extracted with additional methylene chloride and the combined organic phases were were washed with water, dried over sodium sulfate and concentrated. The residue was chromatographed (9:1 methylene chloride/methanol) and the crude product was twice taken up in toluene and concentrated, to provide 2-(1-imidazolyl)-4'-(4-pyridyl)-acetophenone (17.2 g, as yellow crystals. MP 144–146°; NMR (CDCl$_3$) 8.92 (d, 2H), 8.10 (d, 2H), 7.80 (d, 2H), 7.55 (m, 3H), 7.15 (s, 1H), 6.97 (s, 1H); Mass spec 264.

Part C

A solution of 4-bromotrifluoromethylbenzene (8.54 g, 0.038 mol) in tetrahydrofuran (25 mL) was treated dropwise at −78° with n-butyllithium (1.6 M in hexane; 23.7 mL, 0.038 mol) and the mixture was stirred for 30 min. This was then transferred by a cannula to a second flask containing a slurry of cerium chloride (flame-dried under vacuum; 9.35 g, 0.038 mol) in tetrahydrofuran (25 mL) at −78°. The mixture was stirred at −78° for 60 min, then was treated with a solution of the product of Part B (2.0 g, 0.0076 mol) in tetrahydrofuran (30 mL) and the mixture was warmed to room temperature and stirred overnight. Saturated aqueous ammonium chloride (60 mL) was added, the mixture was diluted with water and extracted with methylene chloride. The organic phase was washed with water, dried over sodium sulfate and concentrated. The residue was chromatographed twice (3:1 ethanol/isopropanol, then 9:1 methylene chloride/methanol. Recrystallization (acetonitrile) provided the title compound as off-white crystals (0.50 g, 16%). MP 221-223°; NMR (CDCl$_3$) 8.70 (d, 2H), 7.70 (10H), 7.32 (s, 1H), 6.90 (s, 1H), 6.70 (s, 1H), 6.55 (s, 1H), 4.95 (dd, 2H); Mass spec 410; Calcd. for $C_{23}H_{18}F_3N_3O$: C-67.48, H-4.43, N-10.26, F-13.92; Found: C-67.34, H-4.57, N-10.09, F-14.02.

Additional compounds which may be prepared using the method of Example 21 are shown in Table 2.

TABLE 2

| Ex. # | R$^1$ | R$^9$ | R$^3$ | R$^{10}$ | mp (°C.) |
|---|---|---|---|---|---|
| 21 | 4-CF$_3$-ph | 4-(4-pyr) | 1-imdz | H | 221–223 |
| 22 | 4-Cl-ph | 4-(4-pyr) | 1-imdz | H | 211–213 |
| 23 | 4-C$_4$H$_9$-ph | 4-(4-pyr) | 1-imdz | H | |
| 24[1] | 4-(CHO)-ph | 4-(4-pyr) | 1-imdz | H | 209–211 |
| 25[2] | 4-CH$_3$CO-ph | 4-(4-pyr) | 1-imdz | H | 218–220 |
| 26 | 4-(CH$_2$)$_4$N-ph | 4-(4-pyr) | 1-imdz | H | |
| 27 | 4-(CH$_3$)$_2$N-ph | 4-(4-pyr) | 1-imdz | H | 105–107 d |
| 28 | 2-thiazolyl | 4-(4-pyr) | 1-imdz | H | |
| 29 | 3-thienyl | 4-(4-pyr) | 1-imdz | H | |
| 30 | 2-pyr | 4-(4-pyr) | 1-imdz | H | |
| 31 | 3-pyr | 4-(3-pyr) | 1-imdz | H | |
| 32 | 3-Br-ph | 3-(4-pyr) | 1-imdz | H | |
| 33 | 3,4-(CH$_3$O)$_2$-ph | 4-(2-pyr) | 1-imdz | H | |
| 34 | 4-CH$_3$S-ph | 4-(4-pyr) | 1-imdz | CH$_3$ | |
| 35 | 4-CH$_3$SO$_2$-ph | 4-(3-pyr) | 1-imdz | H | |
| 36 | 4-C$_4$H$_9$O-ph | 3-(4-pyr) | 1-imdz | H | |
| 37 | 3-Cl-4-CH$_3$O-ph | 4-(4-pyr) | 1-imdz | H | |
| 38 | 2,4-F$_2$-ph | 4-(4-pyr) | 1-(1,2,4-tz) | H | |
| 39 | 2-furyl | 4-(3-pyr) | 1-imdz | H | |
| 40 | 2-(N—CH$_3$)-pyrryl | 3-(4-pyr) | 1-imdz | H | |

Footnotes for Table 2
ph = phenyl; pyr = pyridyl; imdz = imidazolyl; tz = triazolyl
[1]Prepared with the aldehyde protected as the dimethyl acetal; the acetal was hydrolyzed on work-up of the reaction.
[2]Prepared with the ketone protected as the dimethyl ketal; the ketal was hydrolyzed with dilute aqueous acid using standard methods.

EXAMPLE 41

Preparation of 1-(4-fluorophenyl)-1-[4-(4-pyridyl)phenyl[1-2-(1-benzimidazolyl)ethanol Part A A solution of 4-fluorophenylmagnesium bromide (prepared from 7.6 ml (0.070 mol) 4-bromofluorobenzene and 3.40 g (0.14 mol) magnesium turnings) in tetrahydrofuran (150 mL) was added to a suspension of 4-(4-acetylphenyl)pyridine (9.85 g, 0.050 mol) in tetrahydrofuran (50 mL) at 0°. The mixture was stirred for 30 min at 0° and for 30 min at room temperature, then was poured into saturated aqueous ammonium chloride. The mixture was extracted with ether, the organic phase was washed with water and brine, then was dried over magnesium sulfate and concentrated. The residue was recrystallized (1-chlorobutane) to give 1-(4-fluorophenyl)-1-[4-(4-pyridyl)phenyl]ethanol colorless needles (10.0 g, 68%). MP 166-170°; NMR (CDCl$_3$) 8.60 (d, 2H), 7.60-7.40 (8H), 7.00 (t, 2H), 2.00 (s, 3H).

A solution of the product of Part A (9.50 g, 0.032 mol) and p-toluenesulfonic acid hydrate (13.00 g, 0.068 mol) in chloroform (250 mL) was heated to boiling. Water and chloroform were removed by distillation, with additional chloroform added to maintain the volume as needed. After 30 min, the mixture was cooled, concentrated to about 100 mL and diluted with ethyl acetate. The solution was washed with 1 M aqueous sodium bicarbonate, water and brine and was dried over magnesium sulfate and concentrated to provide 1-(4-fluorophenyl)-1-[4-(4-pyridyl)phenyl]ethylene (7.4 g, 84%) as a yellow oil. NMR (CDCl$_3$) 8.65 (m, 2H), 7.60-7.25 (8H), 7.00 (t, 2H), 5.50 (d, 2H).

Part C

A solution of the product of Part B (6.30 g, 0.023 mol) in acetone (45 mL) was treated with N-methylmorpholine N-oxide hydrate (3.40 g, 0.025 mol) and water (15 mL). The resulting solution was treated with pyridine (7.5 mL) and a few crystals of osmium tetroxide and was heated at reflux for 24 h. Additional N-methylmorpholine N-oxide hydrate (0.34 g) was added and the solution was heated for an additional 16 h. The mixture was cooled to room temperature, diluted with ethyl acetate and washed with water. The water was back-extracted with ethyl acetate and the combined organic phases were washed with 95:5 water/glycerin, water and brine and dried over magnesium sulfate. The residue was 1-(4-fluorophenyl)-1-[4-(4-pyridyl)phenyl]-2hydroxyethanol (6.8 g, 96%). NMR (CDCl$_3$) 8.50 (d, 2H), 7.60-7.10 (8H), 7.00 (t, 2H), 4.20 (dd, 2H), 2.35 (s, 2H).

Part D

A solution of the product of Part C (0.48 g, 1.52 mmol) in chloroform (8 mL) was treated with triethylamine (1.10 mL, 7.90 mmol). The solution was cooled to −25° and treated with methanesulfonyl chloride (0.15 mL, 1.98 mmol). The mixture was warmed to room temperature and stirred for 45 min. Water was added, the layers were separated and the organic phase was washed with water and brine and was dried over magnesium sulfate and concentrated. The residue was taken up in benzene and concentrated, then was dissolved in N,N-dimethylformamide (7 mL). Benzimidazole (0.314 g, 2.66 mmol) and potassium tert-butoxide (0.298 g, 2.66 mmol) were added and the mixture was heated at 90° overnight. It was cooled to room temperature, diluted with water and extracted with ethyl acetate. The organic phase was washed with water and brine and was dried over magnesium sulfate and concentrated. The residue was chromatographed (95:5 methylene chloride/isopropanol) and the crude product was recrystallized (acetonitrile) to give the title compound (0.283 g, 45%) as a tanyellow powder. NMR (DMSO-d$_6$) 8.60 (m, 2H), 8.85-7.40 (10H), 7.10-7.00 (4H), 6.55 (m, 1H), 5.15 (broad s, 2H); Calcd for $C_{26}H_2OFN_3O \cdot H_2O$: C-74.76, H-5.06, N-10.04; Found: C-74.36, H-4.87, N-10.12.

Additional compounds which may be prepared using the method of Example 41 are shown in Table 3.

TABLE 3

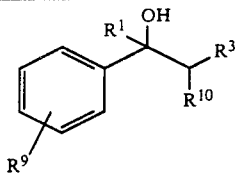

| Ex. # | R¹ | R⁹ | R³ | R¹⁰ | mp (°C.) |
|---|---|---|---|---|---|
| 41 | 4-F-ph | 4-(4-pyr) | 1-bzim | H | 206 |
| 42 | 4-F-ph | 4-(4-pyr) | 1-pyrrolyl | H | 186–187 |
| 43 | 4-F-ph | 4-(4-pyr) | 1-indolyl | H | |
| 44 | 4-F-ph | 4-(4-pyr) | 1-(1,2,4-tz) | H | 119 |
| 45 | 3,4-F₂-ph | 3-(4-pyr) | 1-imdz | H | |
| 46 | 4-F-ph | 4-(4-pyr) | 1-pyrazolyl | H | 164–165 |
| 47 | 4-F-ph | 4-(4-pyr) | 1-bzim | CH₃ | |
| 48 | 2,4-Cl₂-ph | 3-(4-pyr) | 1-imdz | H | |
| 49 | 3,4-Cl₂-ph | 3-(2-pyr) | 1-(1,2,4-tz) | H | |
| 50 | 4-F-ph | 4-(4-pyr) | 1-(1,3,4-tz) | H | |
| 51 | 3-Br-ph | 4-(4-pyr) | 1-(1,2,4-tz) | H | |
| 52 | 2-Cl-ph | 3-(4-pyr) | 1-bzim | H | |
| 53 | 3-CH₃O-ph | 2-(4-pyr) | 1-imdz | H | |
| 54 | 4-F-ph | 2-(4-pyr) | 1-imdz | H | 208 |
| 55 | 4-F-ph | 2-(3-pyr) | 1-imdz | H | 138 |
| 56 | 2,4-F₂-ph | 4-(3-pyr) | 1-(1,2,4-tz) | CH₃ | |
| 57 | 2-thienyl | 3-(3-pyr) | 1-imdz | H | |
| 58 | 2-(1-CH₃-imdz) | 4-(4-pyr) | 1-imdz | H | |
| 59 | 2-F-ph | 4-(4-pyr) | 1-pyrrolyl | H | |
| 60 | 2,4-(CH₃O)₂-ph | 4-(4-pyr) | 1-imdz | H | |
| 61 | 4-OHCH₂-ph | 4-(4-pyr) | 1-imdz | H | 173–175 |
| 62 | 4-CH₃OCO-ph | 4-(4-pyr) | 1-imdz | H | 229–231 |

Footnotes for Table 3
bzim = benzimidazolyl

Examples of the preparation of compounds of formula (I) by functional group manipulation of other compounds of formula (I) are given in Examples 61 and 62.

EXAMPLE 61

Preparation of
1-(4-hydroxymethylphenyl)-4-(4-pyridyl)phenyl]1-2-(1-imidazolyl)-ethanol A solution of the compound of Example 24 (0.20 g, 0.54 mmol) in methanol (25 mL) was treated with sodium borohydride (65 mg, 1.72 mmol) and stirred overnight at room temperature. The solution was concentrated, taken up in water and extracted with ethyl acetate. The extracts were washed with water, dried over magnesium sulfate and concentrated. The residue was chromatographed with 9:1 methylene chloride/methanol to give the title compound as off-white crystals (0.12 g, MP 173–175° C.; NMR (DMSO-d₆) 8.62 (d, 2H), 7.70 (m, 4H), 7.60 (d, 2H), 7.45 (d, 2H), 7.32 (s, 1H), 7.25 (d, 2H), 6.87 (s, 1H), 6.65 (s, 1H), 6.25 (s, 1H), 5.15 (t, 1H), 4.87 (dd, 2H), 4.45 (d, 2H); Mass spec 371; Calcd. for $C_{23}H_{21}N_3O_2$: C-70.95, H-5.90, N-10.79; Found: C-71.13, H-5.89, N-10.30.

EXAMPLE 62

Preparation of
1-(4-methoxycarbonylphenyl)-1-[4-4-pyridyl)phenyl]-2-(1-imidazolyl)-ethanol Using the method of McDonald et al., J. Oro. Chem. 1989, 54, 1213, the compound of Example 24 was converted to the title compound in 65% yield. MP 229–231°; NMR (DMSO-d₆) 8.9 (d, 2H), 8.62 (d, 2H), 7.75 (d, 2H), 7.7–7.6 (6H), 7.3 (s, 1H), 6.85 (s, 1H), 6.65 (s, 1H), 6.5 (s, 1H), 4.92 (dd, 2H), 3.82 (s, 3H); Mass spec 400; Calcd. for $C_{24}H_{21}N_3O_3 \cdot 3H_2O$: C-71.21, H-5.19, N-10.38; Found: C-71.20, H-5.22, N-10.33.

UTILITY

The compounds of Formula (I) have been shown to be efficacious in murine models of skin inflammatory diseases. One such model is inflammation induced by tetradecanoyl phorbol acetate (TPA), modified from the method of Kuehl et al., Nature, 1977, 265, 170; and Van Arman, Clin. Pharmacol. Ther., 1974, 16, 900. The TPA model mimics many of the inflammatory changes which occur in human diseases such as psoriasis, since elevated levels of inflammatory arachidonic acid metabolites are found and an influx of polymorphonuclear leukocytes is observed.

The test procedure used to evaluate the compounds of formula (I) is as follows: the test compound (100 mg/ear) was applied to the ears of mice in an appropriate vehicle, such as acetone, and then TPA, the inflammatory stimulus was applied to the right ear. Four hours later, the edema was measured by removing standard size discs from the ears using a biopsy punch. The weights of the ears were determined, and the suppression of the swelling observed in animals not treated with the test compound was determined. Results obtained in this model for selected compounds of Formula (I) are shown in Table I.

TABLE I

| Example | % inhibition of control swelling |
|---|---|
| 1 | 72 |
| 2 | 51 |
| 3 | 63 |
| 4 | 52 |
| 5 | 73 |
| 6 | 61 |
| 7 | 64 |
| 8 | 69 |
| 9 | 46 |
| 10 | 63 |
| 11 | 62 |
| 12 | 74 |
| 21 | 66 |
| 22 | 79 |

PHARMACEUTICAL COMPOSITIONS

The compounds of the invention are useful in the treatment of inflammatory diseases, including but not limited to rheumatoid arthritis, osteoarthritis, tendonitis, bursitis, psoriasis, contact dermatitis, eczema, inflammatory bowel disease, uveitis and conjunctivitis. Administration of the compounds of this invention can be by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent and its mode and route of administration; age, health and weight of the recipient; nature and extent of symptoms, kind of concurrent treatment, frequency of treatment and the effect desired. Usually a daily dosage of active ingredient can be about 0.1 to 100 milligrams per kilogram of body weight. Ordinarily 0.5 to 50, and preferably 1 to 25 milligrams per kilogram per day given in divided doses 1 to 6 times a day or in sustained release form is effective to obtain desired results.

Compositions (dosage forms) suitable for internal administration contain from about 1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms. It can also be administered by inhalation in the form of a nasal spray or lung inhaler. It can also be administered topically as an ointment, cream, gel, paste, lotion, solution, spray, aerosol, liposome, or patch. Dosage forms used to administer the active ingredient usually contain suitable carriers, diluents, preservatives or other excipients, as described in *Remington's Pharmaceutical Sciences*, 17th Edition (1985) A. Osol, a standard reference text in the field.

Gelatin capsules contain the active ingredient and powdered carriers, such as lactose, sucrose, mannitol, starch, cellulose derivatives, magnesium stearate, stearic acid and the like. Similar diluents can be used to make compressed tablets and powders. Both tablets and capsules can be manufactured as sustained release products to provide for continuous release of medication over a period of hours. Compressed tablets can be sugar coated or film coated to mask any unpleasant taste and protect the tablet from the atmosphere or enteric coated for selective disintegration in the gastrointestinal tract.

Liquid dosage forms for oral administration can contain coloring and flavoring to increase patient acceptance.

In general, water, a suitable oil, saline, aqueous dextrose (glucose) and related sugar solutions and glycols such as propylene glycol or polyethylene glycols are suitable carriers for parenteral solutions. Solutions for parenteral administration contain the active ingredient, suitable stabilizing agents and if necessary, buffer substances. Anti-oxidizing agents such as sodium bisulfite, sodium sulfite or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben and chlorobutanol.

The topical ointments, creams, gels and pastes can contain diluents such as waxes, paraffins, starch, polyethylene glycol, silicones, bentonites, silicic acid, animal and vegetable fats, talc and zinc oxide or mixtures of these or other diluents. Topical solutions and emulsions can, for example, contain the customary diluents (with the exclusion of solvents having a molecular weight below 200 except in the presence of a surface-active agent), such as solvents, dissolving agents and emulsifiers; specific examples are water, ethanol, isopropanol, ethyl carbonate, benzyl alcohol, propylene glycol, oils, glycerol and fatty acid esters of sorbitol or mixtures thereof. Compositions for topical dosing may also contain preservatives or antioxidizing agents.

Powders and sprays can contain the usual diluents, such as lactose, talc, silicic acid, aluminum hydroxide, calcium silicate and polyamide powders or mixtures of these materials. Aerosol sprays can contain the usual propellants. Liposomes can be made from such materials as animal or vegetable fats which will form lipid bilayers in which the active ingredient can be incorporated.

Patches can be made of a matrix such as polyacrylamide and a semipermeable membrane made from a suitable polymer to control the rate at which the material is delivered to the skin.

Examples of useful pharmaceutical compositions for administration of the compounds of this invention can be illustrated as follows:

CAPSULES: A large number of unit capsules are prepared by filling standard two-piece hard gelatin capsules each with 50 mg of powdered active ingredient, mg of lactose, 24 mg of talc and 6 mg of magnesium stearate.

SOFT GELATIN CAPSULES: A mixture of active ingredient in soybean oil is prepared and injected by means of a positive displacement pump into gelatin to form soft gelatin capsules containing 50 mg of the active ingredient. The capsules are washed in petroleum ether and dried.

TABLETS: A large number of tablets are prepared by conventional procedures so that the dosage unit is 50 mg of active ingredient, 6 mg of magnesium stearate, 70 mg of microcrystalline cellulose, 11 mg of cornstarch and 25 mg of lactose. Appropriate coatings may be applied to increase palatability or delay absorption.

SUSPENSION: An aqueous suspension is prepared for oral administration so that each 5 mL contain 25 mg of finely divided active ingredient, 200 mg of sodium carboxymethyl cellulose, 5 mg of sodium benzoate, 1.0 g of sorbitol solution, U.S.P. and 0.025 mg of vanillin.

INJECTABLE: A parenteral composition suitable for administration by injection is prepared by stirring 1.5% by weight of active ingredient in 10% by volume propylene glycol and water. The solution is sterilized by commonly used techniques.

NASAL SPRAY: An aqueous solution is prepared such that each 1 mL contains 10 mg of active ingredient, 1.8 mg methylparaben, 0.2 mg propyl-paraben and 10 mg methylcellulose. The solution is dispensed into 1 mL vials.

LUNG INHALER: A homogeneous mixture of the active ingredient in polysorbate 80 is prepared such that the final concentration of the active ingredient will be 10 mg per container and the final concentration of polysorbate 80 in the container will be 1% by weight. The mixture is dispensed into each can, the valves are crimped onto the can and the required amount of dichlorotetrafluoroethane is added under pressure.

OINTMENT: The active ingredient is added to a mixture of 48% by weight white petrolatum, 10% liquid petrolatum, 8% glycerol monostearate, 3% isopropyl myristate and 20% lanolin at 70° C. After thorough mixing, a warm solution of methyl and propyl parabens in water containing sodium acetone bisulfite is added such that the final concentrations of each paraben is 0.15%, of water is 8%, and of sodium acetone bisulfite is 0.5%. The mixture is stirred until it has reached room temperature.

What is claimed is:

1. A compound of having the formula:

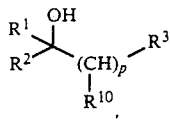

in the form of an individual stereoisomer, a non-racemic stereoisomer mixture or a racemic mixture or a pharmaceutically acceptable salt thereof wherein:

$R^1$ is $R^7$ or phenyl optionally substituted with 1-3 substituents independently selected from the group consisting of F, Cl, Br, $C_1$-$C_4$ alkyl, $C_1$-$C_4$ perfluoroalkyl, $C_1$-$C_4$ alkylthio, $C_1$-$C_4$ alkylsulfonyl, CHO, COOR$^4$, $C_1$-$C_4$ acyl, $NR^5R^6$, $C_1$-$C_4$ alkoxy or $CH_2OR^8$;

$R^2$ and $R^7$ independently are phenyl substituted in the ortho, meta, or para position with $R^9$;

$R^3$ is imidazole;

$R^4$, $F^8$, and $R^{10}$ independently are H or $C_1$-$C_4$ alkyl;

$R^5$ and $R^6$ independently are H, $C_1$-$C_4$ alkyl, or taken together are $(CH_2)_m$ wherein m is 4-5;

$R^9$ is 2-, 3-, or 4-pyridyl; and p is 1-4 provided that when p is greater than 1, then $R^{10}$ is H.

2. A compound of claim 1 wherein p is 1.

3. A compound of claim 1 wherein $R^{10}$ is H.

4. A compound of claim 2 wherein $R^{10}$ is H.

5. A compound of claim 1 wherein $R^1$ is phenyl optionally substituted by one or two substituents independently selected from the group consisting of F, Cl, Br, $C_1$-$C_4$ alkyl, $C_1$-$C_4$ perfluoroalkyl, $C_1$-$C_4$ alkylthio, $C_1$-$C_4$ alkylsulfonyl, CHO, COOR$^4$, $C_1$-$C_4$ acyl, $NR^5R^6$, $C_1$-$C_4$ alkoxy or $CH_2OR^8$.

6. A compound of claim 2 wherein $R^1$ is phenyl optionally substituted by one or two substituents independently selected from the group consisting of F, Cl, Br, $C_1$-$C_4$ alkyl, $C_1$-$C_4$ perfluoroalkyl, $C_1$-$C_4$ alkylthio, $C_1$-$C_4$ alkylsulfonyl, CHO, COOR$^4$, $C_1$-$C_4$ acyl, $NR^5R^6$, $C_1$-$C_4$ alkoxy or $CH_2OR^8$.

7. A compound of claim 1 wherein:
$R^3$ is imidazole;
$R^{10}$ is H; and
$R^1$ is phenyl optionally substituted by one or two substituents independently selected form the group consisting of F, Cl, Br, $C_1$-$C_4$ alkyl, $C_1$-$C_4$ perfluoroalkyl, $C_1$-$C_4$ alkylthio, $C_1$-$C_4$ alkysulfonyl, CHO, COOR$^4$, $C_1$-$C_4$ acyl, $NR^5R^6$, $C_1$-$C_4$ alkoxy or $CH_2OR^8$.

8. A compound of claim 2 wherein:
$R^3$ is imidazole;
$R^{10}$ is H; and
$R^1$ is phenyl optionally substituted by one or two substituents independently selected form the group consisting of F, Cl, Br, $C_1$-$C_4$ alkyl, $C_1$-$C_4$ perfluoroalkyl, $C_1$-$C_4$ alkylthio, $C_1$-$C_4$ alkylsulfonyl, CHO, COOR$^4$, $C_1$-$C_4$ acyl, $NR^5R^6$, $C_1$-$C_4$ alkoxy or $CH_2OR^8$.

9. A compound of claim 7 wherein $R^1$ is mono- or di-substituted phenyl with one of the substituents at the 4-position.

10. A compound of claim 7 wherein $R^2$ is 4-(4-pyridylphenyl) or 3-(4-pyridylphenyl).

11. A compound of claim 7 wherein:
$R^1$ is mono- or di-substituted phenyl with one of the substituents at the 4-position; and
$R^2$ is 4-(4-pyridylphenyl) or 3-(4-pyridylphenyl).

12. The compound of claim 11 which is 1-(4-fluorophenyl)-1-[4-(4-pyridyl)phenyl]-2-(1-imidazolyl)ethanol.

13. The compound of claim 11 which is 1-(2,4-difluorophenyl)-1-[4-(4-pyridyl)phenyl]-2-(1-imidazolyl)ethanol.

14. The compound of claim 11 which is 1-(4-fluorophenyl)-1-[3-(4-pyridyl)phenyl]-2-(1-imidazolyl)ethanol.

15. The compound of claim 11 which is 1-(4-methylphenyl)-1-[4-(4-pyridyl)phenyl]-2-(1-imidazolyl)ethanol.

16. The compound of claim 11 which is 1-(4-methoxyphenyl)-1-[4-(4-pyridyl)phenyl]-2-(1-imidazolyl)ethanol.

17. The compound of claim 11 which is 1-(4-trifluoromethylphenyl)-1-[4-(4-pyridyl)phenyl]-2-(1-imidazolyl)ethanol.

18. The compound of claim 11 which is 1-(4-chlorophenyl)-1-[4-(4-pyridyl)phenyl]-2-(1-imidazolyl)ethanol.

19. A pharmaceutical composition comprising a pharmaceutically acceptable carrier and an anti-inflammatory effective amount of a compound of claim 1.

20. A pharmaceutical composition comprising a pharmaceutically acceptable carrier and an anti-inflammatory effective amount of a compound of claim 2.

21. A pharmaceutical composition comprising a pharmaceutically acceptable carrier and an anti-inflammatory effective amount of a compound of claim 3.

22. A pharmaceutical composition comprising a pharmaceutically acceptable carrier and an anti-inflammatory effective amount of a compound of claim 4.

23. A pharmaceutical composition comprising a pharmaceutically acceptable carrier and an anti-inflammatory effective amount of a compound of claim 5.

24. A pharmaceutical composition comprising a pharmaceutically acceptable carrier and an anti-inflammatory effective amount of a compound of claim 6.

25. A pharmaceutical composition comprising a pharmaceutically acceptable carrier and an anti-inflammatory effective amount of a compound of claim 7.

26. A pharmaceutical composition comprising a pharmaceutically acceptable carrier and an anti-inflammatory effective amount of a compound of claim 8.

27. A pharmaceutical composition comprising a pharmaceutically acceptable carrier and an anti-inflammatory effective amount of a compound of claim 9.

28. A pharmaceutical composition comprising a pharmaceutically acceptable carrier and an anti-inflammatory effective amount of a compound of claim 10.

29. A pharmaceutical composition comprising a pharmaceutically acceptable carrier and an anti-inflammatory effective amount of a compound of claim 11.

30. A pharmaceutical composition comprising a pharmaceutically acceptable carrier and an anti-inflammatory effective amount of the compound of claim 12.

31. A pharmaceutical composition comprising a pharmaceutically acceptable carrier and an anti-inflammatory effective amount of the compound of claim 13.

32. A pharmaceutical composition comprising a pharmaceutically acceptable carrier and an anti-inflammatory effective amount of the compound of claim 14.

33. A pharmaceutical composition comprising a pharmaceutically acceptable carrier and an anti-inflammatory effective amount of the compound of claim 15.

34. A pharmaceutical composition comprising a pharmaceutically acceptable carrier and an anti-inflammatory effective amount of the compound of claim 16.

35. A pharmaceutical composition comprising a pharmaceutically acceptable carrier and an anti-inflammatory effective amount of the compound of claim 17.

36. A pharmaceutical composition comprising a pharmaceutically acceptable carrier and an anti-inflammatory effective amount of the compound of claim 18.

37. A method of treating an inflammatory disease in a mammal comprising administering to the mammal an anti-inflammatory effective amount of a compound of claim 1.

38. A method of treating an inflammatory disease in a mammal comprising administering to the mammal an anti-inflammatory effective amount of a compound of claim 2.

39. A method of treating an inflammatory disease in a mammal comprising administering to the mammal an anti-inflammatory effective amount of a compound of claim 3.

40. A method of treating an inflammatory disease in a mammal comprising administering to the mammal an anti-inflammatory effective amount of a compound of claim 4.

41. A method of treating an inflammatory disease in a mammal comprising administering to the mammal an anti-inflammatory effective amount of a compound of claim 5.

42. A method of treating an inflammatory disease in a mammal comprising administering to the mammal an anti-inflammatory effective amount of a compound of claim 6.

43. A method of treating an inflammatory disease in a mammal comprising administering to the mammal an anti-inflammatory effective amount of a compound of claim 7.

44. A method of treating an inflammatory disease in a mammal comprising administering to the mammal an anti-inflammatory effective amount of a compound of claim 8.

45. A method of treating an inflammatory disease in a mammal comprising administering to the mammal an anti-inflammatory effective amount of a compound of claim 9.

46. A method of treating an inflammatory disease in a mammal comprising administering to the mammal an anti-inflammatory effective amount of a compound of claim 10.

47. A method of treating an inflammatory disease in a mammal comprising administering to the mammal an anti-inflammatory effective amount of a compound of claim 11.

48. A method of treating an inflammatory disease in a mammal comprising administering to the mammal an anti-inflammatory effective amount of the compound of claim 12.

49. A method of treating an inflammatory disease in a mammal comprising administering to the mammal an anti-inflammatory effective amount of the compound of claim 13.

50. A method of treating an inflammatory disease in a mammal comprising administering to the mammal an anti-inflammatory effective amount of the compound of claim 14.

51. A method of treating an inflammatory disease in a mammal comprising administering to the mammal an anti-inflammatory effective amount of the compound of claim 15.

52. A method of treating an inflammatory disease in a mammal comprising administering to the mammal an anti-inflammatory effective amount of the compound of claim 16.

53. A method of treating an inflammatory disease in a mammal comprising administering to the mammal an anti-inflammatory effective amount of the compound of claim 17.

54. A method of treating an inflammatory disease in a mammal comprising administering to the mammal an anti-inflammatory effective amount of the compound of claim 18.

* * * * *